United States Patent [19]

Muth

[11] Patent Number: 4,611,493

[45] Date of Patent: Sep. 16, 1986

[54] PROCESS AND APPARATUS FOR EXECUTING A PLURALITY OF MUTUALLY COMPLEMENTARY MICROSCOPIC INVESTIGATIONS

[75] Inventor: Karl-Heinz Muth, Lollar, Fed. Rep. of Germany

[73] Assignee: Ernst Leitz Wetzlar GmbH, Wetzlar, Fed. Rep. of Germany

[21] Appl. No.: 654,220

[22] Filed: Sep. 25, 1984

[30] Foreign Application Priority Data

Sep. 30, 1983 [DE] Fed. Rep. of Germany ....... 3335480

[51] Int. Cl.⁴ ............................................. G01N 29/04
[52] U.S. Cl. ........................................ 73/606; 73/601; 73/866.1
[58] Field of Search ............. 73/601, 606, 618, 432 A, 73/432 AD; 350/522; 29/36, 35.5; 74/813

[56] References Cited

U.S. PATENT DOCUMENTS

| | | | |
|---|---|---|---|
| 2,244,463 | 6/1941 | Kingsbury et al. | 29/35.5 |
| 2,914,952 | 12/1959 | Frischmann | |
| 3,007,097 | 10/1961 | Shelley et al. | 29/35.5 |
| 3,790,281 | 2/1974 | Kessler et al. | 73/603 |
| 4,011,748 | 3/1977 | Bond et al. | 73/601 |
| 4,190,313 | 2/1980 | Schultz | |
| 4,476,492 | 10/1984 | Muth | |

OTHER PUBLICATIONS

Patents Abstracts of Japan, vol. 7, No. 23 (P-171) [1168], Jan. 29, 1983.

Primary Examiner—Anthony V. Ciarlante
Attorney, Agent, or Firm—Schwartz, Jeffery, Schwaab, Mack, Blumenthal & Evans

[57] ABSTRACT

For carrying out several mutually complementary microscopic examinations, beams of different types or frequencies, for example light beams or acoustic beams, are focused simultaneously or successively on an object and recorded or visibly displayed in a known manner. The object is maintained stationary and is scanned in a grid pattern in two mutually perpendicular directions by at least one of the beams. A pillar arrangement is provided to receive different microscopic instruments which may be selectively pivoted by means of a rotary mounting plate into and out of a locked, exactly reproducible observation position. The instruments may be released for rotation out of the observation position independently of any vertical coarse-fine focusing displacement. Underneath a stationary object holder further microscopic instruments, such as an inverted optical microscope, may be mounted in such a manner that their height may be adjusted. In this fashion, simultaneous optical and acoustic microscope examinations of an object are possible, with the observations being effected from opposite sides of the object.

20 Claims, 6 Drawing Figures

PROCESS AND APPARATUS FOR EXECUTING A PLURALITY OF MUTUALLY COMPLEMENTARY MICROSCOPIC INVESTIGATIONS

BACKGROUND OF THE INVENTION

This invention relates to a process for executing several mutually complementary microscopic investigations of an object and to an apparatus for carrying out the process.

U.S. Pat. No. 4,011,748 discloses a process and an apparatus for acoustic and optical microscopy. The process makes possible both the simultaneous recording of an acoustic and an optical image of an object and the visual observation of it by means of an object detail imaged by an optical lens. The corresponding microscope comprises optical and acoustic systems of lenses, which focus light waves and sound waves in the same focal plane and convert the modulated light rays or acoustic waves reflected by or passing through the object into electric signals. The electric signals are then reproduced on the display screen of a cathode ray tube as a microscopic image of the object. The object is scanned and in the process moved through the focal plane in a grid pattern, which is synchronized with the cathode ray tube. It is also possible to leave the object stationary. In this case the entire microscope must be moved in the grid pattern with a drive synchronous with that of the cathode ray tube. By using a beam divider, the object image on the cathode ray tube may also be observed as in a conventional optical microscope. During reproduction of an image on the display screen of the cathode ray tube such a direct visual observation is not possible, because of the movement of the object or of the entire system in the grid pattern.

U.S. Pat. No. 3,790,281 discloses a combined system for simultaneous acoustical-optical investigation of a stationary object using a scanning laser beam and sonic waves. Because of the use of unfocused waves, no appreciable enlargement is possible with this apparatus. Furthermore, a partially reflecting and elastically deformable intermediate surface connected with the object is required to produce a specific wave pattern. The optical scanning of said wave pattern then produces an acoustical image, while no acoustical scanning takes place.

Japanese Utility Model application No. 56-22,172 describes a microscopic apparatus comprising an optical and an acoustical microscope, mounted fixedly on a base plate. Reversing means are provided between them, so that optical and acoustic microscopic observations may be effected successively. No simultaneous investigation by means of optical and acoustical objectives arranged on the same side of the object is possible with this apparatus because acoustical imaging requires a scanning motion performed by the object.

Finally, it is known (LEITZ-Mitt. Wiss. u. Techn. Vol. VIII, No. ¾, pp. 61–67, Wetzlar, May 1982), to combine an acoustical scanning microscope with a reflected light microscope. This arrangement comprises a substructure with an object stage and an oscillator system with an acoustic objective that may be pivoted vertically into its operating position, and an incident light microscope mounted on a horizontally pivotable support. The latter may be brought into the working position over the object in place of the oscillator system with the acoustic objective. The acoustic and the optical microscopes are aligned with each other so that details of the object selected by the optical microscope may be found again subsequently in the acoustic microscopic image with scarcely any deviation. In the course of the necessary grid scanning of the object by means of the ultrasonic focus, the rapid movement in the linear direction of the grid is correlated with the objective of constant mass and the slow, stepwise motion perpendicular to the linear direction is correlated with the object stage with the object having a variable mass. No simultaneous optical examination of the latter is thus possible with this configuration.

SUMMARY OF THE INVENTION

It is the object of the present invention to provide a process for executing a plurality of mutually complementary microscopic investigations of an object which makes effective use of different types or frequencies of radiation.

A further object of the present invention is to provide a process for executing a plurality of mutually complementary microscopic investigations of an object in which complementary examinations of the precise same details of the object may be performed without repositioning the object on the object holder or moving the object holder.

An additional object of the present invention is to provide a process for carrying out a plurality of mutually complementary microscopic investigations of an object in which proper correlation of the results of the different examinations is facilitated.

It is also an object of the present invention to provide apparatus for carrying out several mutually complementary microscopic investigations of an object.

In a first aspect of the invention the objects are achieved by providing a process for carrying out a plurality of mutually complementary microscopic investigations of an object comprising producing first and second beams of radiation, said second beam differing from said first beam; focusing said first and second beams on the object to be investigated; scanning the object being investigated in a grid pattern in two mutually perpendicular directions, said scanning being effected by moving the source of one of said beams of radiation while maintaining the object being investigated and the source of the other beam of radiation stationary; and visibly displaying the results of the investigations.

In a further aspect of the invention the objects are achieved by providing an apparatus for carrying out a plurality of mutually complementary microscopic investigations of an object comprising means for generating a first beam of radiation, means for generating a second beam of radiation differing from said first beam of radiation, means for focusing said first and second beams of radiation onto the object being investigated, means for moving one of said beams of radiation in a grid pattern to scan the object being investigated in two mutually perpendicular directions, and means for visibly displaying the results of the investigations.

In a particularly preferred embodiment of the invention, apparatus is utilized which comprises a pillar mounted on a base plate and carrying a rotary plate parallel to said base plate, said rotary plate being adjustable in height and being provided with at least two receptacles for first and second microscopic instruments having parallel axes of observation spaced an equal distance from the axis of rotation of said rotary plate, said rotary plate being selectively rotatable to pivot a desired one of said microscopic instruments into an observation position aligned with an object holder for the object being investigated, means for selectively locking a desired microscopic instrument in the observation position, the observation axis of each of said microscopic instruments occupying the same position with respect to said object holder when that microscopic instrument is rotated to said observation position.

The process of the invention comprises producing at least two beams of different types or frequencies by means of appropriate sources of radiation, focusing the beams simultaneously or successively on the object under investigation, and visibly displaying the results by known means; the stationary object being scanned in a grid pattern in two mutually orthogonal directions while only one type of radiation source is moved.

As different types of radiation in particular, light rays, laser beams and ultrasonic waves may be used. Thus, a beam of light and an acoustic beam may be produced on the same side of the object, with the focused beam of light serving to select a detail of the object and to examine it under incident or transmitted light, and the object detail subsequently being scanned in two perpendicular directions (i.e., in a grid pattern) by the acoustic beam and then visibly displayed following conversion of the scanning result into electric signals. It is further possible to successively produce two acoustic beams of different frequencies on the same side of the object and focus them while scanning an area of the object, whereby acoustic images of different resolution are obtained. For simultaneous optical and acoustical microscopic examination and image generation, an optical beam and an acoustical beam may be generated on opposite sides of the object and focused simultaneously on the same detail of the object, as the object always remains stationary and only the acoustic beam executes the scanning motion. In a further embodiment of the process of the invention, a laser beam and an acoustic beam may be generated on opposite sides of the object and focused simultaneously on the same detail of the object to examine it. In this embodiment, the source of the laser beam may be stationary and the scanning motion achieved by directing the laser beam at a reversing element synchronized with the scanning movement of the acoustic beam. In this manner, dilatometric measurements and examinations of objects combined with acoustical microscope observations may be made visible.

The invention further relates to an apparatus for carrying out a plurality of mutually complementary microscopic investigations of an object, comprising a pillar mounted vertically on a base plate and carrying a rotary plate which is adjustable in height and is parallel to the base plate. The rotary plate comprises at least two receptacles for different microscopic instruments, the axes of observation of which are parallel to and spaced apart from the axis of rotation of the rotary plate. Within the pivoting range of the axes of observation on the base plate, an object holder is provided at a distance from it, and means are provided for selectively locking the rotary plate in positions wherein the examination instruments when pivoted into said positions always occupy the same position with respect to the object holder.

This apparatus makes it possible by means of certain fundamental structural groups functionally correlated with each other to execute a series of different microscopic investigative procedures, both simultaneously and successively, wherein because of the stationary arrangement of both the objects and the object holders, their weight and dimensions may vary within wide limits, and the location or identification of certain details of the object may be readily effected with great precision by means of simple bearings and detents or locks.

The pillar may suitably consist of two U shaped elements between which a vertically displaceable slide with a coarse-fine displacement adjustment is located, said slide being connected with the U shaped elements via a prestressed roller guide. In addition to rapid coarse adjustment, movement of the slide without play and with extremely short adjusting paths is thereby possible in any position of the slide.

In one preferred embodiment of the apparatus of the invention, the rotary plate is rotatably supported in the slide and may be released from a locked operating position by raising it together with the slide, independently of the coarse-fine adjustment of the latter. In this manner, damage to the objectives or objects is reliably prevented, since rotary motion of the rotary plate is possible only after it has been moved together with the slide upwardly out of its working position. The cleaning and wetting of the acoustic objectives with an immersion liquid is also effected in this outwardly pivoted position.

In a further embodiment of the invention a support is provided on the base plate with an adjustable height guide to mount at least one further microscopic examination apparatus which is associated with the underside of the object holder. Depending on the arrangement of the appropriate microscopic instruments on the support guide and in the receptacles of the rotary plate, a plurality of investigations may be performed and combinations effected, as demonstrated by the following examples:

1. Individual optical microscope investigations (a) To locate and bring into focus a certain detail of the object as well as for supplementary interpretation of an acoustic image, an incident light optical microscope may be placed in a receptacle of the rotary plate which is cooperation with a corresponding illuminating device is capable of producing images in a conventional manner by the bright field, dark field, polarizing, fluorescent and interference contrast processes.

(b) For transmitted light investigations a microscope may be inserted in the receptacle of the rotary plate over the object plane and different condensers mounted on the support guide underneath the object plane in combination with an illuminating device, again resulting in the known processes of bright field, dark field, polarization and interference microscopy.

(c) For both incident light and transmitted light investigations, a microscope may be arranged on the support guide underneath the object holder and coordinated with it. The microscope may be used in combination with an illuminating device inserted in a receptacle of the rotary plate for transmitted light investigations, or with an opaque illuminator for incident light examinations. For adjustments in height for focusing, the reversed microscope may be moved in its entirety by means of a coarse-fine adjustment of the support guide.

2. Individual acoustic microscope investigations (a) For acoustic microscopic examination of an object by the reflection process, wherein a detail of the object optionally has first been selected or identified by optical means, an acoustic microscope instrument head is set into a receptacle of the rotary plate, together with an acoustic objective. The acoustic objective serves both as a source of radiation and as the receiver for the focused ultrasonic waves and requires systematic grid-like scanning of the detail of the object in order to generate an image. The configuration and mode of operation of acoustic microscopes are known.

An important feature of the invention is that the scanning of the object, which is stationary during the imaging exposure, is effected in all of the acoustic microscope investigations exclusively by moving the acoustic objective in two perpendicular directions by means of a device referred to hereinafter as an x-y oscillator. Such a device is described in DE-OS No. 31 35 180 (corresponding to U.S. Pat. No. 4,476,492), the disclosure of which is incorporated herein by reference.

The x-y oscillator comprises an inner oscillator system for the y direction and an outer oscillator system for the x direction of the acoustic objective. The inner oscillator system is in the form of a symmetrical steering gear, which moves an acoustic objective fixedly joined to it along a straight line. The vibrations occurring at high frequencies are compensated by dynamic mass equalization, with the movements of the counter mass occurring offset in phase by 180° with respect to the oscillator motion. For the stepped x movement of the acoustic objective a spring parallelogram oscillator is provided. The two oscillator systems may be driven by immersion coil vibrators, wherein in view of the greater mass that must be moved by an exact amount during the reversal of the inner oscillator system, a stronger vibrator or two vibrators may be used for the outer oscillator system. Photoemitter and photodifference diodes are used to control the drive systems. By means of this oscillator apparatus, first, the magnitude of the movement may be adjusted with great precision using a measuring system in combination with the steering means, and second, it may be assured that the stepwise movement takes place during the reversal in direction of the oscillating motion.

(b) If two acoustic microscope instrument heads with objectives for different ultrasonic frequencies are inserted in the receptacles of the rotary plate, the apparatus of the invention may switch rapidly between acoustic microscope exposure with high resolution and a slight depth of penetration and exposures with a low resolution and a great depth of penetration. It was found that this change may be performed with a positioning accuracy of ±5 μm, whereby examinations and evaluations actually take place on exactly the same detail of the object. With appropriately small manufacturing tolerances, the replacement of the acoustic objectives may also be effected directly, using the same x-y oscillator.

3. Simultaneously optical and acoustical microscope investigations (a) Simultaneous optical and acoustical investigations may be performed if an acoustic microscope instrument head is inserted in a receptacle of the rotary plate and an optical microscope having a reverse configuration is mounted on the support guide underneath the plane of the object. The object to be examined is arranged in the object holder and positioned by means of an x-y adjustment of the object holder. During the investigation the object holder, and thus the object, remains stationary and the object is scanned in a grid-like fashion by the acoustic objective as described above. The fine adjustment of the slide is used for accurately setting the depth of penetration of the acoustic examination under the surface of the object. The optical microscope examination is effected with incident light, and all of the imaging processes listed under 1(a) are possible.

(b) Of course, if desired, the optical microscope may also be inserted in a receptacle of the rotary plate and the acoustic miscroscope instrument head may be arranged on the support guide.

4. Further variants (a) The simultaneous use of two acoustic microscope instrument heads makes possible investigations by the transmission process. The instrument head arranged on one side of the object may serve as the emitter for the ultrasonic waves and the head on the other side may serve as the receiver. In the process, two x-y oscillators are operated synchronously to move the two acoustic heads in synchronized fashion.

(b) In place of the light optical imaging system according to 3(a) to (b) a laser pulse device may also be used, whereby photoacoustical investigations may be performed. Such investigations are described in detail in European Pat. No. 12,262, the disclosure of which is incorporated herein by reference. The laser device may be mounted on the support guide or if a reversed microscope is used, in a tubular receptacle on the support. In both cases the source of radiation for the laser beam remains stationary and the scanning in a grid pattern by the laser beam is achieved by means of a reversing element, for example a scanning mirror, the movements of which are synchronized with those of the x-y oscillator. Each time an acoustical signal is obtained from a detail of the object, this detail is also exposed to a laser pulse.

Suitable means for displaying and recording the microscopic images obtained by the different processes include known oscillographic display systems with luminescent screens and analog or digital image memories in combination with standard television monitors.

BRIEF DESCRIPTION OF THE DRAWINGS

Further details of the invention will become apparent from the following description of several illustrative embodiments shown schematically in the drawings wherein.

DETAILED DESCRIPTION OF PREFERRED EMBODIMENTS

Figure 1:
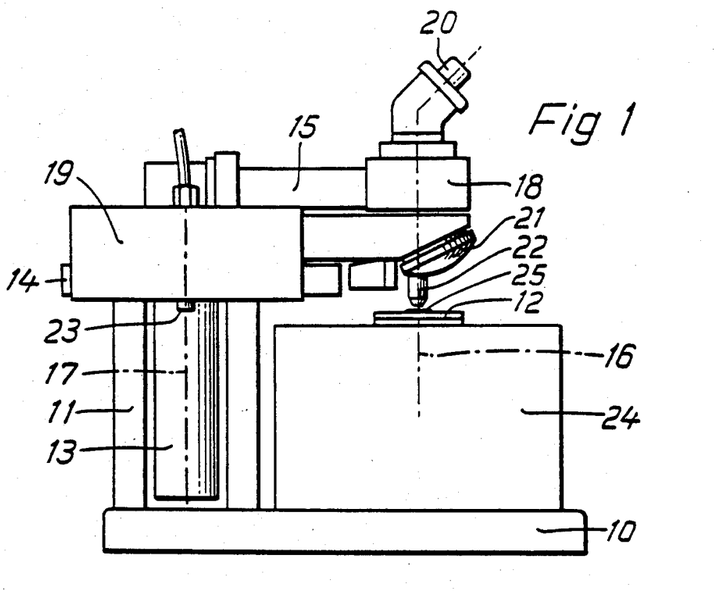
FIG. 1 shows a simplified side elevation of a first embodiment of the apparatus of the invention for carrying out successive optical and acoustical investigations.
Figure 2:
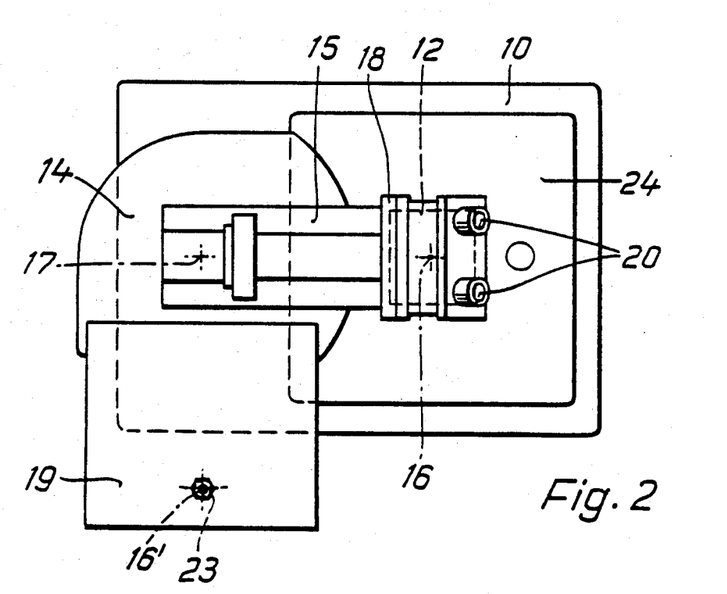
FIG. 2 is a top view of the apparatus of FIG. 1.

In the illustrative embodiment shown in FIGS. 1 and 2, a pillar 11 consisting of two U shaped elements and an object holder 12 are mounted on a base plate 10. Pillar 11 forms the guide for a vertically displaceable slide 13 which carries a rotary plate 14 by means of structural elements to be described hereinafter in more detail, with the plane of the rotary plate parallel to the base plate 10. A plurality of receptacles 15, each offset by 90°, are provided in locking positions (only one shown) in the rotary plate 14 for receiving different microscopic examination instruments, with the viewing axes 16, 16' of said instruments parallel to and identically spaced from the axis of rotation 17 of the rotary plate 14. In this embodiment, optical apparatus 18 pivoted into the operating position for incident light examinations and an outwardly pivoted acoustical microscope apparatus 19 for subsequent observation of reflected ultrasonic waves are mounted in the receptacles 15. The optical microscope apparatus 18 is of the generally known type comprising a binocular tube 20 and an objective 22 secured to a lens turret 21 and requires no detailed description. The same is true for the acoustic microscope apparatus 19 with an acoustic objective 23, whereby the apparatus 19 contains as essential parts the oscillator and its drive, and the objective 23 serves simultaneously as the emitter and the receiver for the ultrasonic waves.

The object holder 12 is mounted on a support frame 24 mounted on the base plate 10 and serves to hold and position an object 25 in an x-y coordinate field. Depending on the application, different types of known object stages may be employed, such as for example standard or rotary and centering mechanical stages with coordinate and angle value memories. The optical stages may have receptacle boreholes for heating stages, and they may be driven manually or by motors.

Figure 3:
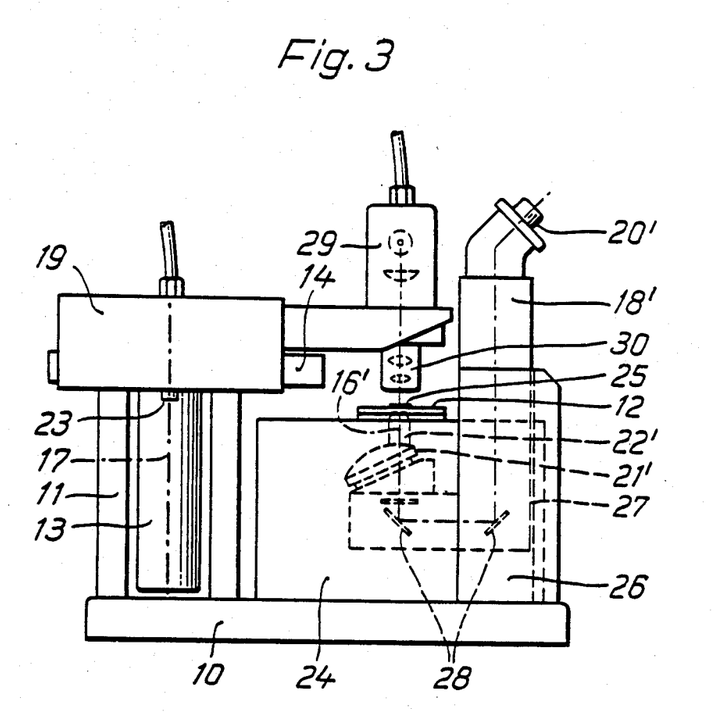
FIG. 3 depicts another illustrative embodiment with a reversed optical microscope.

The illustrative embodiment shown in FIG. 3 differs from that of FIGS. 1 and 2 essentially in the layout of the optical microscope apparatus 18'. The binocular tube 20' is mounted on the base plate 10 and may be displaced up and down in a guide 27 by means of a coarse-fine adjustment, not shown. The lens turret 21' with the objective lens 22' is located in the free space within the support frame 24 under the object holder 12. Mirrors 28 are arranged in the viewing axis 16' in a known manner. An illuminating device 29 with a condenser 30 is mounted in one receptacle 15 of the rotary plate 14 in the operating position, while the acoustic microscopic apparatus 19 in the other receptacle 15' is pivoted out of the operating position. This layout permits optical microscope investigations using both incident and transmitted light, while subsequent acoustic microscope observations are also possible.

Figure 4:
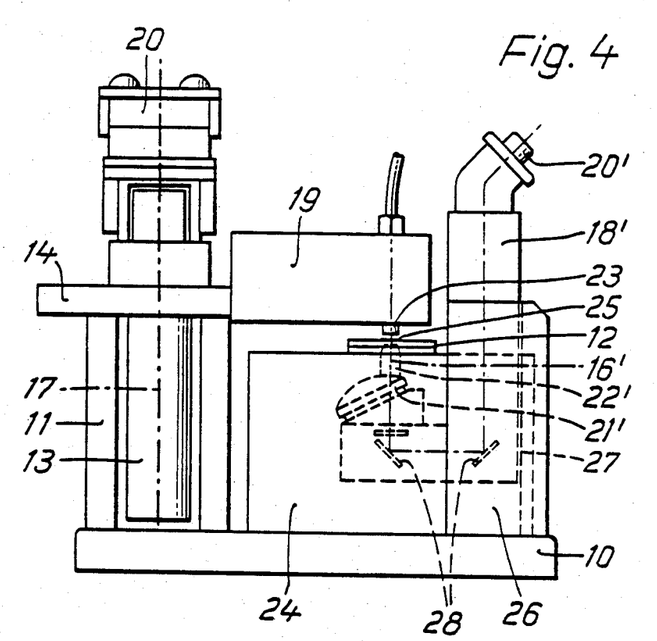
FIG. 4 shows a simplified side elevation of a third illustrative embodiment for carrying out simultaneous optical and acoustical microscope investigations.

In the illustrative embodiment shown in FIG. 4, the optical microscope apparatus 18' is also an inverted microscope. However, for simultaneous acoustic microscope investigations the acoustic microscope apparatus 19, together with its drive, not shown, for x-y scanning of the object 25 by means of the acoustic objective 23 as described above, is pivoted into its operating position and thus placed on the opposite side.

Figure 5:
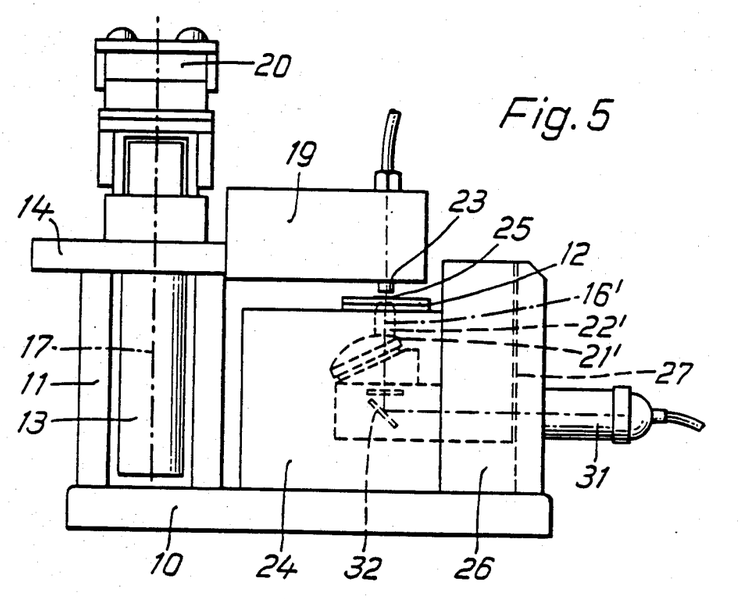
FIG. 5 shows a fourth illustrative embodiment using a laser device.

Photoacoustic investigations are feasible with the layout shown in FIG. 5. In place of the inverted optical microscope apparatus 18', in this illustrative embodiment a laser device 31 is arranged in the pillar 26 in a height adjustable manner, with the acoustic microscope apparatus 19 located on the opposite side of the object 25 in a simultaneous operating position. The pulsed laser beam emitted by laser device 31 is reflected by a scanning mirror 32 onto the bottom of the object 25, with the scanning mirror 32 being synchronized with the oscillating motion in the acoustic microscope apparatus 19, so that with the laser device 31 stationary, a simultaneous grid pattern scanning of the object 25 is effected by the laser pulses.

Figure 6:
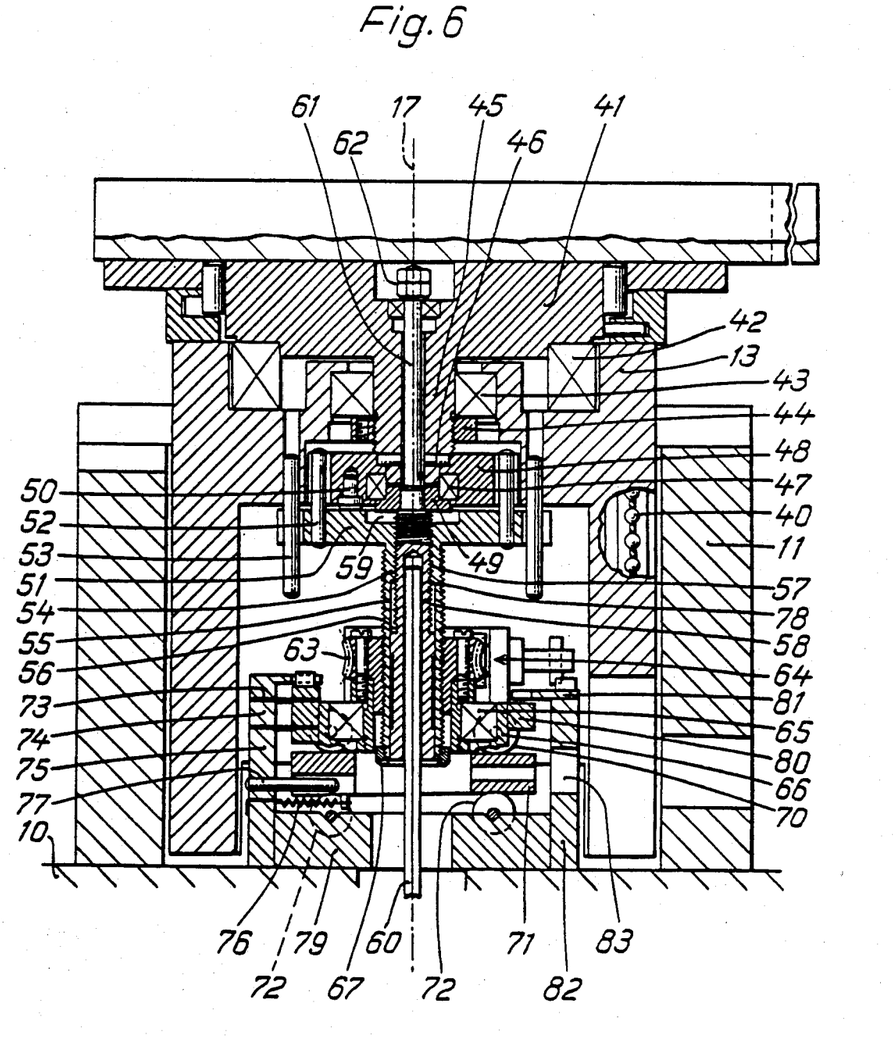
FIG. 6 is a sectional view of the basic mechanical configuration of an adjusting means for the apparatus of the invention.

In the apparatus shown sectionally in FIG. 6, the base plate 10 is shown with the pillar 11 mounted on it, with the slide 13 guided vertically inside the pillar. To avoid play, prestressed roller bearings 40 are used. A flange 41 is rotatably mounted on slide 13 by means of a taper roller bearing 43 and a threaded ring 44. The flange 41 is fixedly attached to the rotary plate 14 carrying the receptacles 15, 15' for the microscopic instruments, not shown here, for example by screws, and is equipped with a downwardly extending cylindrical fitting 45 which is fixedly connected by means of a driving pin 46 and a ball bearing 47 with a bearing ring 48 so that the two rotate together. The ball bearing 47 is supported by support ring 49. A plurality of support pins 50 are inserted in the bearing ring 48, by means of which the bearing ring is supported on a plate 51. Vertical lock pins 52 are inserted in the plate 51 and extend with their upper portions into the bearing ring 48. Additional elongated pins 53 are disposed between the slide 13 and the plate 51 and penetrate plate 51 in the area of its periphery.

The plate 51 is provided with a downwardly extending cylindrical extension 54 comprising external threads 55 and a central bore 56 having internal threads 57 in its upper section. A spindle 58 is guided in bore 56 and is adjustable vertically in the internal threading 57. The upper end of the spindle 58 protrudes from an annular recess 59 in the center of the plate 51 and abuts the lower surface of the support ring 49. Within the spindle 58 a hexagonal shaft 60 is arranged coaxially. Shaft 60 is further extended downward through the base plate 10 and may be driven manually or by a motor in a manner not shown in detail.

The cylindrical extension at the top of the spindle 58 extends further through the flange 41 in the form of a central shaft 61 with its lower end mounted in mounting ring 49 and with its upper end supported in the flange 41 and held therein by two opposing nuts 42.

A worm wheel 63 engages the external threads 55 of the cylindrical extension 54, said worm wheel being mounted in a bearing element 66 such that it can be rotated via a ball bearing 65 by means of a screw 64, thereby supporting the plate 51. The lower end of extension 54 carries a threaded ring 67.

Further upper ball bearings 70 are fastened in the bearing element 66, said bearings 70 resting with their outer ring on top of a slightly tapering slide element 71, which in turn is supported by lower ball bearings 72 and is thereby displaceable horizontally by means of an outside drive, not shown. The bearing element 66 is secured and guided in one end of the leaf spring paralellogram 73, which at its other end is held by intermediate plates 74 on a vertical support 75 mounted on base plate 10. To facilitate movement of the slide element 71 without play, a tension spring 76 is fastened to the slide element, the other end of the spring engaging the support 75. Linear guidance of the slide element 71 is effected by a guide pin 77 inserted therein, said pin 77 being fastened with its other end in the support 75.

The following description of the manner of operation of the pillar arrangement begins with the rotary plate 14 in the operating position shown in FIG. 6. In this position no pivoting motion of the rotary plate 14 is possible, as on the one hand the bearing ring 48 is fixed against relative rotation with respect to the flange 41 by means of driving pin 46 and on the other hand, the bearing ring 48 is secured by the vertical lock pins 52 against rotation. In this manner, contact between or damage to the objectives and the object being investigated due to pivoting of the rotary plate 14 is reliably prevented. Both the coarse and fine adjustments of the apparatus are effected in this working position.

The rapid vertical adjustment for pivoting the rotary plate 14 between locking positions at 90° intervals is effected by driving the hexagonal shaft 60, whereby the spindle 58 in the bore 56 is rotated upwardly in the internal threads 57 of the cylindrical extension 54. In the process, the support ring 49 with the ball bearing 47, the bearing ring 48 with the driver pin 46, the flange 41 with the threaded ring 44, the axial and roller bearings 42, 43 and thus the slide 13 and the rotary plate 14 are raised at the same time. The release position is attained when the lower edge of the bearing ring 48 is disposed above the upper edge of the lock pins 52, whereupon the upward motion of the spindle 58 and of the above-mentioned structural parts is limited by an internal stop 78 in the bore 56 of the extension 54. In this position the rotary plate 14 may be pivoted around the center shaft 61 in the flange 41 within the slide 13 in the axial bearing 42 and the tapered roller bearing 43 into a locking position offset by 90°. During pivoting of the rotary plate, relative rotation between the slide 13 and the plate 51 is reliably prevented by means of the elongated pins 53 arranged therebetween.

Downward movement of the rotary plate 14 is possible only in one of the locking positions since in the intermediate positions the bottom of the bearing ring 48 impacts against the lock pins 52, thereby preventing downward motion of the aforementioned structural parts. After the rotary plate 14 has reached a new locking position, it is lowered together with the structural elements 13 and 41-49 by driving the hexagonal shaft 60 in the opposite direction, whereupon the lock pins 52 again receive the bearing ring 48, and the initially described condition is restored. The lower stop for this downward movement is provided by the support pins 50, which contact the plate 51.

Coarse adjustments for the purpose of prefocusing are effected in one of the locking positions by actuating the drive screw 64, the drive of which extends from outside the pillar and may be activated manually or by a motor (not shown). By actuation of the screw 64 the worm wheel 63 fastened in the bearing element 66 is rotated in the ball bearing 65 and is moved vertically in the slide 13 by engaging the external threads 55 on the extension 54 of the plate 51. Plate 51 transmits the movement through the support pins 50 to the bearing ring 48, the flange 41 and the rotary plate 14 and thus to the microscopic apparatus. In the present case the vertical coarse adjustment permits a rise of 40 mm. The amount of rise is limited by a stop constituted by the threaded ring 67 and the lower surface of the worm wheel 63.

For fine adjustments by means of a drive, not shown, for example by means of a threaded spindle and a nut, the slightly tapered slide element (71) is horizontally displaced between the upper ball bearings 70 fastened in the bearing element 66 and the lower ball bearings 72 arranged on a plate 79 mounted on the base plate 10. The tension spring 76 is provided to assure movement of the slide element 71 without play, and the guide pin 77 is provided for linear guidance of slide element 71. A vertical movement of the bearing element 66 is associated with the horizontal movement of the slide element 71, bearing element 66 being fastened to the flat spring parallelogram 73. The vertical motion of the bearing element 66 is transmitted, as in coarse adjusting, through the plate 51 and the bearing ring 48 to the flange 41 and the rotary plate 14. The fine adjustment is limited in the upward direction by a stop rail 80 mounted on the bearing element 66, and a cover plate 81 is fastened to the upper end of a support plate 82. The drive for the fine adjustment extends to the outside through an opening 83 in support 82. The fine adjustment permits a rise of ±0.1 mm with a resolution of 0.1 μm.

The course-fine adjustment described above may also be used for vertical movement of microscopic instruments fastened in the guide 27 of the pillar 26 and associated with the bottom of the object holder 12. In place of this coarse-fine adjustment on separate shafts, both the coarse and the fine adjustments may be performed in a known manner on a common shaft. In the case of further automation and particularly if motor drives are used, limit switches may be employed in place of the described stops.

The foregoing description has been set forth merely to illustrate the invention and is not intended to be limiting. Since modifications of the described embodiments incorporating the spirit and substance of the invention may occur to persons skilled in the art, the scope of the invention is to be limited solely with respect to the appended claims and equivalents.

What is claimed is:

1. A process for carrying out a plurality of mutually complementary microscopic investigations of a stationary object comprising:
   producing first and second beams of radiation, said second beam differing from said first beam;
   focusing said first and second beams on the object to be investigated;
   scanning the object being investigated in a grid pattern in two mutually perpendicular directions, said scanning being effected by moving the source of one of said beams of radiation while maintaining the object being investigated and the source of the other beam of radiation stationary; and
   visibly displaying the results of the investigations.

2. A process according to claim 1, wherein said first and second beams of radiation comprise different types of radiation.

3. A process according to claim 2, wherein one of said beams of radiation comprises a beam of light and the other of said beams of radiation comprises an acoustic beam.

4. A process according to claim 1, wherein said first and second beams of radiation comprise beams of the same type of radiation which differ in frequency from each other.

5. A process according to claim 1, wherein one of said beams of radiation is a beam of light which is focused on the object being investigated, and light emanating from the object being investigated is viewed through an optical objective, and said second beam of radiation comprises an acoustic beam focused on the same side of the object as said light beam, said beams of radiation being focused in succession on said object being examined; said acoustic beam scanning the detail of the object being examined in two mutually perpendicular directions.

6. A process according to claim 1, wherein one of said beams of radiation comprises a beam of light focused on one side of the object being investigated for subsequent transmitted light examination, and transmitted light emanating from the opposite side of the object being investigated is viewed through an optical objective; the other of said beams of radiation comprising an acoustic beam focused on the opposite side of the object being examined from said light beam, said beams of radiation being focused successively on the object being investigated, and said acoustic beam scanning the detail of the object being investigated in two mutually perpendicular directions.

7. A process according to claim 1, wherein two acoustic beams having different frequencies are produced and focused on the same side of the object being investigated, and one of said acoustic beams scans the object being investigated in two mutually perpendicular directions.

8. A process according to claim 1, wherein one of said beams of radiation is a beam of light and the other of said beams of radiation is an acoustic beam, said beams being produced and focused simultaneously on opposite sides of the object being investigated, said acoustic beam scanning details of the object being investigated in two mutually perpendicular directions.

9. A process according to claim 1, wherein one of said beams of radiation comprises a laser beam and the other of said beams of radiation comprises an acoustic beam, said beams of radiation being produced and focused simultaneously on opposite sides of the object being investigated, said acoustic beam directly scanning details of the object being investigated in two mutually perpendicular directions, and said laser beam being reflected to scan the same details of the object being investigated synchronously with the acoustic beam.

10. Apparatus for carrying out a plurality of mutually complementary microscopic investigations of a stationary object comprising:
   means for generating a first beam of radiation;
   means for generating a second beam of radiation differing from said first beam of radiation;
   means for focusing said first and second beams of radiation onto the object being investigated;
   means for moving one of said beams of radiation in a grid pattern to scan the stationary object being investigated in two mutually perpendicular directions; and
   means for visibly displaying the results of the investigations.

11. Apparatus according to claim 10, comprising a pillar mounted on a base plate and carrying a rotary plate parallel to said base plate, said rotary plate being adjustable in height and being provided with at least two receptacles for first and second microscopic instruments having parallel axes of observation spaced an equal distance from the axis of rotation of said rotary plate, said rotary plate being selectively rotatable to pivot a desired one of said microscopic instruments into an observation position aligned with an object holder for the object being investigated, means for selectively locking a desired microscopic instrument in the observation position, the observation axes of said microscopic instruments occupying the same position with respect to said object holder when the microscopic instrument is rotated to said observation position.

12. Apparatus according to claim 11, further comprising a second pillar mounted on said base plate, guide means for mounting a further microscopic instrument on said pillar positioned to observe the underside of an object resting on said object holder, and means for adjusting the height of said guide means.

13. Apparatus according to claim 12, wherein said further microscopic instrument is selected from the group consisting of illuminating means, a laser, an acoustic microscope objective, and an optical microscope objective forming an inverted optical microscope.

14. Apparatus according to claim 11, wherein two different microscopic instruments selected from the group consisting of an optical microscope, illuminating means, a laser, and an acoustic microscope are mounted in the receptacles of said rotary plate.

15. Apparatus according to claim 14, wherein one of said microscopic instruments comprises an acoustic microscope connected to a drive system for linearly scanning an object being investigated.

16. Apparatus according to claim 11, wherein said rotary plate is securely joined to a flange member, and said flange member and a bearing ring fixed against rotation relative to said rotary plate are rotatably mounted about a central shaft on a support ring of said slide, said bearing ring being selectively movable vertically between a locked position in which it contacts a support plate and a released position said support plate being provided with a cylindrical vertical extension having a spindle threadedly mounted therein coaxial with said central shaft, the upper end of said spindle engaging said support ring, and vertical movement of said bearing ring between said locked and said released positions being effected by rotating said threadedly mounted spindle.

17. Apparatus according to claim 16, wherein said cylindrical vertical extension of said support plate is provided with external threads, said threads carrying an annular worm gear, and said worm gear being rotatably mounted on a bearing element and rotatable by means of a drive screw.

18. Apparatus according to claim 10, wherein said pillar comprises two U-shaped elements having a vertically movable slide mounted between them by means of prestressed roller bearings, said rotary plate being carried on said slide, and means for effecting coarse and fine adjustments of the vertical position of said slide and rotary plate.

19. Apparatus according to claim 18, further comprising means for rapidly adjusting said rotary plate between a first position in which it is locked against rotation relative to said slide and a second position in which it may be rotated relative to said slide, said rapid adjustment means operating independently of said coarse and fine adjustment means.

20. Apparatus according to claim 18, wherein a slightly tapered horizontally displaceable slide element is provided between upper ball bearings fastened to a bearing element and lower ball bearings fastened to said base plate, said bearing element being held in a desired horizontal position by a leaf spring parallelogram, one end of said parallelogram being attached to said bearing element and the other end of said parallelogram being attached to a support mounted on said base plate.

* * * * *